United States Patent
Kudo (10) Patent No.: US 10,175,217 B2
(45) Date of Patent: Jan. 8, 2019

(54) METHOD FOR RECOVERY METAL AND METAL RECOVERY REAGENT

(71) Applicant: ARKRAY, Inc., Kyoto (JP)

(72) Inventor: Akitsugu Kudo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/632,217

(22) Filed: Feb. 26, 2015

(65) Prior Publication Data

US 2015/0247834 A1 Sep. 3, 2015

(30) Foreign Application Priority Data

Feb. 28, 2014 (JP) ................................ 2014-039592
Feb. 26, 2015 (JP) ................................ 2015-036117

(51) Int. Cl.
*G01N 33/20* (2006.01)
*G01N 33/493* (2006.01)
*G01N 33/48* (2006.01)

(52) U.S. Cl.
CPC ........... *G01N 33/20* (2013.01); *G01N 33/493* (2013.01)

(58) Field of Classification Search
CPC ...... G01N 33/20; G01N 33/00; G01N 33/493; G01N 33/487; G01N 33/483; G01N 33/48
USPC .................................................... 436/81, 73
See application file for complete search history.

(56) References Cited

U.S. PATENT DOCUMENTS

| | | | | |
|---|---|---|---|---|
| 5,126,272 A | * | 6/1992 | Kingston, Jr. | G01N 1/405 210/656 |
| 5,575,915 A | * | 11/1996 | Nakamura | C02F 1/5236 210/631 |
| 5,766,478 A | * | 6/1998 | Smith | B01D 61/16 210/638 |
| 8,232,105 B1 | * | 7/2012 | Scott | G01N 33/84 422/430 |
| 2008/0318248 A1 | * | 12/2008 | Thorp, Jr. | C12Q 1/00 435/7.1 |
| 2012/0251390 A1 | * | 10/2012 | Shimomura | G01N 1/4044 422/68.1 |
| 2013/0017613 A1 | | 1/2013 | Kaminski et al. | |

FOREIGN PATENT DOCUMENTS

| | | | |
|---|---|---|---|
| CN | 103018082 A | 4/2013 | |
| EP | 2261656 A1 | 12/2010 | |
| EP | 2508863 A2 | 10/2012 | |
| EP | 2508864 A2 | 10/2012 | |
| EP | 2572806 A1 | 3/2013 | |
| JP | S52-56070 A | 5/1977 | |
| JP | 2969226 B2 | 11/1999 | |
| JP | 2010 156619 | * 7/2010 | ............... G01N 1/10 |
| JP | 2013-079932 A | 5/2013 | |
| WO | 01/34856 A1 | 5/2001 | |

OTHER PUBLICATIONS

Extended European Search Report issued in corresponding European Patent Application No. 15157195.7 dated Jul. 20, 2015.
"Mercury Analysis Manual," Ministry of the Environment, Japan (2004).
Final Office Action issued in related U.S. Appl. No. 14/632,145 dated May 18, 2016.
Advisory Action issued in related U.S. Appl. No. 14/632,145 dated Aug. 22, 2016.
Office Action issued in corresponding European Patent Application No. 15157195.7 dated Dec. 23, 2016.
Non-Final Office Action issued in related U.S. Appl. No. 14/632,145 dated Jan. 10, 2017.
Final Office Action issued in related U.S. Appl. No. 14/632,145 dated Jul. 7, 2017.
Office Action issued in related European Patent Application No. 15157195.7 dated Oct. 16, 2017.
Office Action issued corresponding Chinese Patent Application No. 201510091692.X dated Feb. 9, 2018.
Office Action issued in corresponding Japanese Patent Application No. 2015-036117 dated May 22, 2018.

* cited by examiner

*Primary Examiner* — Christine T Mui
(74) *Attorney, Agent, or Firm* — Morgan, Lewis & Bockius LLP (57) ABSTRACT

A method for recovering a metal, capable of suppressing variations in complex recovery yields among samples is described, wherein the method comprises: forming a complex between a metal in a sample and a chelating agent for metal in a mixture containing the sample and the chelating agent; and filtering the mixture in the presence of an inorganic salt to recover the complex, thereby recovering the metal in the sample.

12 Claims, 2 Drawing Sheets

METHOD FOR RECOVERY METAL AND METAL RECOVERY REAGENT

TECHNICAL FIELD

The present invention relates to a method for recovering a metal and a metal recovery reagent.

BACKGROUND ART

It is known that metals such as mercury, cadmium, and lead are accumulated in human bodies, which results in adverse effects on health. Therefore, it is important to analyze metals in biological samples such as urine and the like and samples of food and beverages such as water and the like.

In the analysis of metals, generally, foreign substances are removed from a sample as a pretreatment to remove a metal(s), and the separated metal(s) is analyzed. As the pretreatment, a solvent extraction is widely used. The solvent extraction is a method in which a metal in a sample is extracted into an organic medium by utilizing the polarity of a chelating agent to be bound to the metal according to the difference between the distribution coefficient of the metal in an aqueous medium and in the organic medium. The metal can be further concentrated by evaporating the organic medium from the extracted fraction. As a specific example of the solvent extraction, a dithizone method using, as the chelating agent, 1,5-diphenyl-3-thiocarbazone (hereinafter, also referred to as "dithizone") that is insoluble in an aqueous medium under acidic conditions is described in JIS, for example (see Non Patent Literature 1 and Patent Literature 1). In the dithizone method, dithizone and a liquid sample are first mixed under acidic conditions to form a complex between the dithizone and a metal in the liquid sample in the mixture. Subsequently, an organic medium such as carbon tetrachloride or chloroform is added to the mixture. Accordingly, the complex is extracted in the organic medium because the distribution coefficient of the complex in the aqueous medium is different from that of the complex in the organic medium. By recovering this extracted fraction in the organic medium, the metal can be recovered from the liquid sample as a complex. The metal can be further concentrated by further evaporating the organic medium from the extracted fraction.

CITATION LIST

Patent Literature

Patent Literature 1: Japanese Patent No. 2969226

Non Patent Literature

Non Patent Literature 1: Mercury Analysis Manual, Ministry of the Environment, March 2004

SUMMARY OF INVENTION

Technical Problem

As described above, in the method for recovering a metal utilizing the formation of a complex between a chelating agent such as dithizone and a metal, the inventors of the present invention formulated a novel method for recovering the complex by filtering the mixture containing the complex without extracting the complex into the organic solvent. However, the inventors of the present invention identified the problem of variability in complex recovery yields among samples where the complex is recovered by filtration, even through the process to generate the complex is performed under the same conditions. These variations in recovery yields among samples may result in insufficient reliability on the quantitative determination of a metal in a complex under the same conditions.

The present invention is therefore intended to provide a method for recovering a metal, which is capable of suppressing variations in complex recovery yields among samples.

Means for Solving Problem

In order to achieve the aforementioned objective, the method for recovering a metal of the present invention includes: a complex forming step of forming a complex between a metal in a sample and a chelating agent for metal in a mixture containing the sample and the chelating agent; and a metal recovering step of filtering the mixture to recover the resulting complex, thereby recovering the metal in the sample, and in the metal recovering step, the mixture is filtrated in the presence of an inorganic salt.

The method for analyzing a metal of the present invention includes: a metal recovering step of recovering a metal from a sample by the method of the present invention; and an analyzing step of analyzing the metal.

The metal recovery reagent of the present invention is for use in the method for recovering a metal of the present invention and contains: a chelating agent for metal; and an inorganic salt.

Advantageous Effects of the Invention

As a result of their studies, the inventors of the present invention observed that the above-mentioned variations in recovery yield among samples are caused by leakage of the formed complex passing through a filter medium, and depends on the sample even if a process is performed under the same conditions. The inventors of the present invention also observed that the complex leakage during filtration can be suppressed by causing an inorganic salt to be present together in a mixture at the time of the filtration and thus achieved the present invention, although the mechanism is unknown. According to the present invention, the observed variations in recovery yields among samples, such as described above, can be suppressed by suppressing the complex leakage. Moreover, when applied to a sample with a low recovery yield, the recovery yield can be improved, for example. Therefore, a metal can be analyzed with further superior reliability. Thus, the present invention is useful in clinical examinations of samples derived from biological bodies and for environmental testing, for example.

DESCRIPTION OF EMBODIMENTS

<Method for Recovering Metal>

As described above, the method for recovering a metal of the present invention includes: a complex forming step of forming a complex between a metal in a sample and a chelating agent for metal in a mixture containing the sample and the chelating agent; and a metal recovering step of filtering the mixture to recover the complex, thereby recovering the metal in the sample, and in the metal recovering step, the mixture is filtrated in the presence of an inorganic salt. The method for recovering a metal of the present invention (hereinafter referred to as "the metal recovery method of the present invention") is characterized in that the mixture is filtrated in the presence of the inorganic salt in the metal recovering step, with other steps and conditions are not limited.

According to the metal recovery method of the present invention, as mentioned above, the complex recovery leakage can be suppressed by causing an inorganic salt to be present together in filtration of a mixture. It is assumed that this occurs because an aggregate of a complex becomes large by causing an inorganic salt to be present together in a mixture subjected to filtration, which results in suppression of complex leakage. Moreover, according to the metal recovery method of the present invention, for example, a filter with a relatively large pore size can be used because an aggregate of a complex becomes large. Furthermore, according to the metal recovery method of the present invention, although the mechanism is unknown, by causing an inorganic salt to be present together, foaming generated in the mixture can be suppressed, so that handleability is improved. Thus, the present invention is suitable also for automation of metal recovery.

In the metal recovery method of the present invention, a metal to be recovered is not particularly limited. Examples of the metal include heavy metals such as Bi (bismuth), Hg (mercury), Cd (cadmium), Pd (palladium), Zn (zinc), Tl (thallium), Ag (silver), and Pb (lead) and may further include metals such as As (arsenic) and Al (aluminium). The form of the metal in the sample is not particularly limited and may be, for example, a single metal, an alloy of metals, or a metal-containing compound. The metal-containing compound may be, for example, a metal-containing organic compound or a metal-containing inorganic compound. In the case where the metal is Hg, the Hg may be, for example, organic mercury or inorganic mercury. In the metal recovery method of the present invention, the metal to be recovered may be, for example, one kind or two or more kinds. In the metal recovery method of the present invention, two or more kinds of metal can be recovered from a sample in parallel by a single recovery process, for example.

The sample to which the metal recovery method of the present invention is applied is not particularly limited. Examples of the sample include a sample derived from a biological body, a sample derived from the environment, a chemical substance, and a pharmaceutical. Examples of the chemical substance include reagents, pesticides, and cosmetics. The sample derived from a biological body is not particularly limited, and examples thereof include urine, blood, hair, and umbilical cords. Examples of the blood sample include erythrocytes, whole blood, sera, and plasma. Among them, a urine sample is preferable. The sample derived from the environment is not particularly limited, and examples thereof include an organism, food, water, the ground, the atmosphere and air. The organism sample is not particularly limited, and examples thereof include animals such as fish and shellfish, and plants. The food sample is not particularly limited, and examples thereof include a fresh food and a processed food. The water is not particularly limited, and examples thereof include drinking water, groundwater, river water, seawater, and domestic sewage.

The concentration of metal in the sample is not particularly limited and is, for example, in the range from 0.1 to 1000 µg/L, preferably from 0.1 to 200 µg/L, and more preferably from 0.1 to 100 µg/L.

A fluid sample (liquid sample) is preferable as the sample because it can be handled easily, for example. An undiluted liquid sample as is or a diluted liquid sample obtained by suspending, dispersing, or dissolving the sample in a medium may be used as the liquid sample, for example. In the case where the sample is a solid, a diluted sample obtained by suspending, dispersing, or dissolving the sample in a medium may be used as the liquid sample, for example. Hereinafter, the medium is referred to as a dilution medium. The dilution medium is not particularly limited, and examples thereof include water and a buffer solution. The buffer solution is not particularly limited, and examples thereof include a tris buffer solution, a phosphate buffer solution, an acetate buffer solution, a borate buffer solution, a citrate buffer solution, a veronal buffer solution, and various Good buffer solutions. The concentration of the buffer solution is not particularly limited and is, for example, from 10 to 100 mmol/L.

The inorganic salt for use in the metal recovery method of the present invention is not particularly limited, and examples thereof include chloride and hydro sulfate. In the metal recovery method of the present invention, one kind of an inorganic salt may be used, or two or more kinds of an inorganic salt may be used in combination, for example.

The chloride is not particularly limited and can be, for example, metal chloride. The metal in the metal chloride is not particularly limited, and examples thereof include an alkali metal and an alkaline earth metal. Examples of the alkali metal include Li (lithium), Na (sodium), K (potassium), Rb (rubidium), Cs (cesium), and Fr (francium). Examples of the alkaline earth metal include Be (beryllium), Mg (magnesium), Ca (calcium), Sr (strontium), Ba (barium), and Ra (radium). Specific examples of the metal chloride include potassium chloride, magnesium chloride, lithium chloride, sodium chloride, rubidium chloride, cesium chloride, francium chloride, beryllium chloride, calcium chloride, strontium chloride, barium chloride, and radium chloride.

The hydrosulfate is not particularly limited, and examples thereof include metal hydrosulfate and ammonium sulfate. The metal is not particularly limited and can be described with reference to the description of the metal in the metal chloride, for example. Specific examples of the metal hydrosulfate include sodium sulfate, potassium sulfate, lithium sulfate, magnesium sulfate, and beryllium sulfate.

In the complex forming step, the chelating agent is, for example, preferably a chelating agent having a sulfur-containing group. The sulfur-containing group is a functional group having a sulfur atom. The sulfur-containing group is, for example, preferably a thioketone group. The thioketone group is not particularly limited, and examples thereof include a thiocarbazone group, a thiosemicarbazone group, a thiocarbadiazone group, a thiourea group, a thiosemicarbazide group, and a rubeamate group. In the metal recovery method of the present invention, the chelating agents may be used alone or in a combination of two or more, for example.

The chelating agent is, for example, preferably, a chelating agent represented by the following structural formula (4).

(4)

In the structural formula (4), $R^1$ and $R^2$ each represents a phenyl group. That is, the chelating agent represented by the structural formula (4) is a chelating agent having a thiocarbazone group and can be 1,5-diphenyl-3-thiocarbazone (dithizone). The structural formula (4) may represent a salt, for example.

Any hydrogen in the phenyl group may be substituted, for example. For example, the hydrogen in the phenyl group may be substituted by halogen or an alkali metal such as, sodium, or potassium when substituted.

In the complex forming step, the chelating agent is, as mentioned above, preferably a chelating agent having a sulfur-containing group. The sulfur-containing group can be, for example, a thioketone group, and the chelating agent having a thioketone group can be, for example, a chelating agent having at least one group selected from the group consisting of a thiocarbazone group, a thiosemicarbazone group, a thiocarbadiazone group, a thiourea group, a thiosemicarbazide group, and a rubeamate group. Specific examples of the chelating agent having a sulfur-containing group include the following chelating agents. In the present invention, the following chelating agents are mere examples, and the present invention is not limited thereby.

(a1) Chelating agent having a thiocarbazone group
e.g., 1,5-di(2-naphthyl)thiocarbazone;

(a2) Chelating agent having a thiosemicarbazone group
e.g., acetone thiosemicarbazone, acetophenone thiosemicarbazone;

(a3) Chelating agent having a thiocarbadiazone group
e.g., diphenylthiocarbadiazone;

(a4) Chelating agent having a thiourea group
e.g., 1-acetyl-2-thiourea, guanyl thiourea, 1,3-bis(dimethylaminopropyl)-2-thiourea, tetramethyl thiourea, N,N'-diethyl thiourea, N,N'-diisopropyl thiourea, N,N'-dibutyl thiourea, 1,3-bis(dimethylaminopropyl)-2-thiourea, N-allyl-N'-(2-hydroxyethyl)thiourea, N,N'-bis(2-hydroxyethyl)thiourea, diacetyl thiourea, phenyl thiourea, N,N'-diphenyl thiourea, mono-o-tolyl thiourea, N,N'-di-o-tolyl thiourea, benzoyl thiourea;

(a5) Chelating agent having a thiosemicarbazide group
e.g., phenylthiosemicarbazide, 4-phenylthiosemicarbazide, 4-methylthiosemicarbazide, thiosemicarbazide;

(a6) Chelating agent having a rubeamate group
e.g., dithiooxamide (rubeanic acid).

In the complex forming step, the mixture may further contain a masking agent. In the present invention, "masking" means inactivating the reactivity of a SH group and can be performed by a chemical modification of a SH group, for example. The masking agent is not particularly limited, and for example, a known masking agent can be used and includes a SH inhibitor. The chemical modification is not particularly limited, and examples thereof include alkylation, addition to an active double bond, allylation, an exchange reaction with disulfide, oxidation, cyanidation, and mercaptidation.

As the masking agent, a compound represented by at least one structural formula selected from the group consisting of the following structural formulae (1) to (3) can be used, for example. The compounds represented by the following chemical formulae (1) to (3) may be used alone or in a combination of two or more, for example.

(1)

(2)

(3)

In the structural formula (1), R represents, for example, hydrogen, an alkyl group, a phenyl group, or a benzyl group. In the structural formula (2), R represents, for example, hydrogen, an alkyl group, a phenyl group, or a benzyl group, and X represents halogen. In the structural formula (3), R represents, for example, hydrogen, an alkyl group, a phenyl group, or a benzyl group, and X represents halogen.

The alkyl group is not particularly limited, and examples thereof include straight-chain or branched alkyl groups and aromatic alkyl groups. The carbon number of the alkyl group is, for example, from 1 to 7, preferably from 1 to 6, more preferably from 1 to 2, yet more preferably 2. Examples of the straight-chain or branched alkyl groups include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a n-heptyl group, a n-octyl group, a n-nonyl group, and a n-decyl group. Any hydrogen in the alkyl group may be substituted or unsubstituted, for example.

Any hydrogen in the phenyl group and the benzyl group may be substituted or unsubstituted, for example. Examples of the halogen include fluorine, chlorine, bromine, and iodine.

Examples of the masking agent represented by the structural formula (1) include maleimide, N-methyl maleimide, N-ethyl maleimide, N-phenyl maleimide, and maleimide-propionic acid, and the masking agent is preferably N-ethyl maleimide. The compounds represented by the structural formula (1) may be used alone or in a combination of two or more.

The masking agent represented by the structural formula (2) can be, for example, halogenacetamide such as iodoacetamide and is preferably iodoacetamide. The compounds represented by the structural formula (2) may be used alone or in a combination of two or more.

The masking agent represented by the structural formula (3) can be, for example, halogen acetic acid such as iodoacetic acid and is preferably iodoacetic acid. The compounds represented by the structural formula (3) may be used alone or in a combination of two or more.

In the complex forming step, the order of adding the sample and the chelating agent is not particularly limited. In the metal recovery method of the present invention, the inorganic salt may be mixed in the mixture in advance in the complex forming step or may be added to the mixture before the filtration of the mixture after the complex forming step, for example. In the former case, the order of adding the sample, the chelating agent, and the inorganic salt is not particularly limited. As a specific example, for example, the inorganic salt may be further mixed after mixing the sample and the chelating agent, the chelating agent may be further mixed after mixing the sample and the inorganic salt, or the sample, the chelating agent, and the inorganic salt may be mixed simultaneously. In the latter case, the sample and the chelating agent may be mixed to form a complex in the mixture, and the inorganic salt may be thereafter mixed therein, and the mixture may be then subjected to the metal recovering step.

In the complex forming step, the order of adding the masking agent is not particularly limited. Specifically, the masking agent may be mixed before or after mixing the sample and the chelating agent or may be mixed in parallel with mixing the sample and the chelating agent.

In the complex forming step, the composition ratio of the mixture is not particularly limited. The proportion (v/v %) of the sample in the mixture is not particularly limited and is, for example, 50% or more, preferably 80% or more, more preferably 90% or more. The proportion of an undiluted sample in the mixture is preferably in the above-described range.

The concentration of the inorganic salt in the mixture is not particularly limited and is, for example, in the range from more than 0 mol/L to 8 mol/L or less, preferably from 1 mol/L or more to 8 mol/L or less, from 2 mol/L or more to 8 mol/L or less, more preferably from 3 mol/L or more to 8 mol/L or less. The concentration of the inorganic salt may be a concentration of one kind of the inorganic salt or a total of the concentrations of two or more kinds of the inorganic salt.

The mixing ratio between the inorganic salt and the sample in the mixture is not particularly limited, and the amount of the inorganic salt to be mixed is, for example, in the range from more than 0 mmol to 8 mmol or less, preferably from 1 mmol or more to 8 mmol or less, from 2 mmol or more to 8 mmol or less, more preferably from 3 mmol or more to 8 mmol or less relative to 1 mL of the sample.

The concentration of the chelating agent in the mixture is not particularly limited and is, for example, in the range from 0.0025 to 0.3 mg/mL, preferably from 0.005 to 0.3 mg/mL, and more preferably from 0.005 to 0.1 mg/mL. The concentration of the chelating agent may be, for example, a concentration of one kind of the chelating agent or a total of the concentrations of two or more kinds of the chelating agent.

The mixing ratio of the chelating agent and the sample in the mixture is not particularly limited, and the amount of the chelating agent to be mixed is, for example, in the range from 0.0025 to 0.3 mg, preferably from 0.005 to 0.3 mg, and more preferably from 0.005 to 0.1 mg relative to 1 mL of the sample.

The concentration of the masking agent in the mixture is not particularly limited and is, for example, in the range from 0.5 to 30 mg/mL, preferably from 0.5 to 20 mg/mL, and more preferably from 0.5 to 10 mg/mL. The concentration of the masking agent may be a concentration of one kind of the masking agent or a total of the concentrations of two or more kinds of the masking agent.

The mixing ratio of the masking agent and the sample in the mixture is not particularly limited, and the amount of the masking agent to be mixed is, for example, in the range from 0.5 to 30 mg, preferably from 0.5 to 20 mg, and more preferably from 0.5 to 10 mg relative to 1 mL of the sample.

In the present invention, for example, the complex recovered in the metal recovering step may be regarded as the metal, or the metal may be isolated by removing the chelating agent from the recovered complex. In the latter case, the metal recovering step may further include a complex recovering step of recovering the complex by filtrating the mixture and a metal isolating step of isolating the metal from the complex.

In the metal recovering step, a filter medium for use in the filtration in the metal recovering step is not particularly limited and is, for example, a filter medium having a pore(s) and is, preferably a filter. The kind of the filter is not particularly limited, and examples thereof include a filter paper, a woven fabric, a nonwoven fabric, a porous body, and a mesh. The material of the filter is not particularly limited, and examples thereof include glass, a polymer, and cellulose. Examples of the filter include a glass filter such as a glass fiber filter paper, a polymer filter such as a polymer porous body, and a filter paper such as cellulose. The glass filter is not particularly limited, and examples thereof include Standard14 (produced by GE Healthcare Japan), GF/D (produced by GE Healthcare Japan), and GF/B (produced by GE Healthcare Japan). The polymer filter is not particularly limited, and examples thereof include FC-1006 (produced by Japan Vilene Company) and OR-125 (produced by Japan Vilene Company).

The kind of the filter medium and the number of the filter media, to be used in the filtration in the metal recovering step, are not particularly limited. The kind of the filter medium to be used may be, for example, one or two or more in combination. The number of the filter media to be used may be, for example, one or two or more in combination.

The size of the pore(s) in the filter medium is not particularly limited. The pore can also be referred to as a pore size, particle retention capacity, an aperture, and a weight per area. The pore size is not particularly limited and is, for example, in the range from 1 to 90 μm, preferably from 1 to 50 μm, and more preferably from 1 to 30 μm. The particle retention capacity means a particle size with which 98% of all particles to be passed through a filter can be retained and is, for example, in the range from 1 to 90 μm, preferably from 1 to 50 μm, and more preferably from 1 to 30 μm. The size of the aperture is not particularly limited, and is, for example, from 0.001 to 0.09 mm, preferably from 0.001 to 0.05 mm, and more preferably from 0.001 to 0.03 mm.

For example, according to the present invention, a complex leakage can be prevented by using a filter medium with a pore(s) of 1 to 90 μm, even if the sample causes the complex leakage in using filter medium which has a pore(s) in the above-described range in filtration in the absence of the inorganic salt. Moreover, according to the filter medium with a pore(s) in this range, clogging can be further prevented compared with the case where a filter medium with a pore(s) that is smaller than this range is used, for example.

A method for measuring the size of the pore(s) in the filter medium is not particularly limited, and for example, a known method according to the kind of the filter medium can be employed, and the size can be measured by a bubble point method, for example.

The metal recovery method of the present invention is described below with reference to embodiments. The present invention, however, is not limited by these embodiments.

(1) First Embodiment

The metal recovery method of the first embodiment shows an example where a chelating agent represented by the structural formula (4) is used as a chelating agent, and a metal is recovered by recovering a complex through filtration of a mixture in the presence of an inorganic salt.

In the metal recovery method of the present embodiment, the complex forming step includes the following step (1A), and the metal recovering step includes the following step (1B) and optionally includes the steps (1C) and (1D). (1A) a complex forming step of preparing a mixture of a sample and a chelating agent under the pH conditions where the cheating agent is insoluble in an aqueous medium to form a complex between a metal in the sample and the chelating agent;
(1B) a complex recovery step of filtering the mixture in the presence of an inorganic salt, thereby recovering the complex;
(1C) a complex dissolving step of dissolving the recovered complex in an aqueous medium under alkaline conditions;
(1D) a metal isolating step of isolating the metal from the complex.

According to the present embodiment, as mentioned above, a metal can be recovered easily by utilizing the difference in solubility of the chelating agent in an aqueous medium according to the difference in pH conditions without substantially using an organic medium in addition to the suppression of the complex recovery leakage.

(1A) Complex Forming Step

In the complex forming step, a mixture of a sample and a chelating agent is prepared under pH conditions where the chelating agent is insoluble in an aqueous medium to form a complex between a meatal in the sample and the chelating agent in the mixture. Hereinafter, the "pH conditions where the chelating agent are insoluble in an aqueous medium" is also referred to as the "insoluble pH conditions".

The chelating agent can maintain the state of not being dissolved in the mixture under insoluble pH conditions. Therefore, when a metal is present in the sample, a complex between the chelating agent and the metal in the sample is formed in the mixture. The chelating agent is, for example, preferably in a state of being completely undissolved in the mixture and, however, may be in a state of being partially dissolved in the mixture. In the latter case, for example, even in the case where the chelating agent is partially dissolved in the mixture, it is only necessary that the amount of the remaining chelating agent being present in the mixture in the state of not being dissolved therein is the amount capable of forming a complex with the metal.

In the complex forming step, the insoluble pH conditions are not particularly limited. The insoluble pH conditions can be, for example, acidic conditions (pH 5 or less), neutral conditions (pH 6 to 7), or alkaline conditions (more than pH 7 to pH 8 or less). The upper limit of the insoluble pH conditions is, for example, pH 8, preferably pH 6.8, more preferably pH 4, and yet more preferably pH 3, particularly preferably pH 2. The lower limit of the insoluble pH conditions is not particularly limited and is, for example preferably pH 1. The insoluble pH conditions can be set appropriately according to the kind of the chelating agent to be used.

The mixture containing a sample and a chelating agent is not limited as long as it is substantially an aqueous medium. The aqueous medium is a non-organic medium and means an aqueous liquid body. The "substantially aqueous medium" encompasses an aqueous medium containing a slight amount of an organic medium (organic solvent) in addition to an absolute aqueous medium, for example.

When the chelating agent is mixed with the sample, the form of the chelating agent is not particularly limited and may be in a dry state (or also referred to as a solid state) or a liquid state, for example. In the latter case, the chelating agent is preferably a dispersion liquid of the chelating agent, obtained by dispersing the chelating agent in a non-organic medium in which the chelating agent is not dissolved. Hereinafter, a non-organic medium in which the chelating agent is dispersed is also referred to as a "dispersion medium". The dispersion medium is, for example, a non-organic medium (aqueous medium) under the insoluble pH conditions. In the case where the insoluble pH conditions are acidic conditions, examples of the dispersion medium include an acid, an aqueous acid solution, and a buffer solution under acidic conditions. In the case where the insoluble pH conditions are alkaline conditions, examples of the dispersion medium include an alkali, an aqueous alkali solution, and a buffer solution under alkaline conditions. In the case where the insoluble pH conditions are neutral conditions, examples of the dispersion medium include an acid, an aqueous acid solution, a buffer solution under acidic conditions, an alkali, an aqueous alkali solution, and a buffer solution under alkaline conditions in addition to water, an aqueous neutral solution, and a buffer solution under neutral conditions.

The acid is not particularly limited, and examples thereof include hydrochloric acid, sulfuric acid, acetic acid, boric acid, phosphoric acid, and citric acid. Examples of the aqueous acid solution include solutions obtained by diluting an acid with water or a buffer solution. The buffer solution for use in the dilution of acid is not particularly limited, and any of the above-mentioned common buffer solutions can be used. The concentration of acid in the aqueous acid solution is not particularly limited and is, for example, more than 0N to 1N or less, preferably from 0.01N to 0.1N. The buffer solution under acidic conditions is not particularly limited, and examples thereof include a citrate buffer solution, an acetate buffer solution, a phosphate buffer solution, and Good's buffers. The concentration of the buffer solution is not particularly limited and is, for example from 10 to 100 mmol/L.

The aqueous neutral solution is not particularly limited, and examples thereof include a saline solution, a phosphate buffer solution, and a tris buffer solution. The buffer solution under the neutral condition is not particularly limited. The concentration of the buffer solution is not particularly limited and is, for example, from 10 to 100 mmol/L.

The alkali is not particularly limited, and examples thereof include sodium hydroxide and potassium hydroxide. Examples of the aqueous alkaline solution include solutions obtained by diluting an alkali with water or a buffer solution. The buffer solution for use in the dilution of alkali is not particularly limited, and any of the above-mentioned common buffer solutions can be used. The concentration of alkali in the aqueous alkali solution is not particularly limited and is, for example, more than 0N to $7 \times 10^{-3}$N or less. The buffer solution under the alkaline conditions is not particularly limited, and examples thereof include Tris-NaOH, Tris-HCl, a carbonate buffer, and Good's buffers. The concentration of the buffer solution is not particularly limited and is, for example, from 10 to 100 mmol/L.

A method for mixing the sample and the chelating agent is not particularly limited, and examples thereof include the following methods (x) to (z).
(x) mixing a sample adjusted to be under the insoluble pH conditions in advance and a chelating agent;
(y) mixing a chelating agent adjusted to be under the insoluble pH conditions in advance and a sample;
(z) mixing a non-organic medium under the insoluble pH conditions, a chelating agent, and a sample.

In (x), for example, a mixture under the insoluble pH conditions can be prepared by mixing a sample adjusted to be under the insoluble pH conditions and a chelating agent, and in the mixture, a complex can be formed. At that time, for example, the pH of the sample is adjusted so that the mixture prepared by mixing with the chelating agent is under the insoluble pH conditions.

In the case where the insoluble pH conditions are acidic conditions, a method for adjusting the sample to be under acidic conditions is not particularly limited, for example. The adjustment may be performed by adding an acidic reagent to the sample, for example. Examples of the acidic reagent include an acid, an aqueous acid solution, and a buffer solution under acidic conditions. The acid is not particularly limited, and examples thereof include hydrochloric acid, sulfuric acid, citric acid, boric acid, phosphoric acid, and acetic acid. Examples of the aqueous acid solution include solutions obtained by diluting an acid with water or a buffer solution. The buffer solution for use in the dilution of acid is not particularly limited, and any of the above-mentioned common buffer solutions can be used. The concentration of acid in the aqueous acid solution is not particularly limited and is, for example, from 0.01N to 5N. The buffer solution under acidic conditions is not particularly limited, and examples thereof include a citrate buffer solution, an acetate buffer solution, a phosphate buffer solution, and Good's buffers. The concentration of the buffer solution is not particularly limited and is, for example from 10 to 100 mmol/L.

In the case where the insoluble pH conditions are alkaline conditions, a method for adjusting the sample to be under alkaline conditions is not particularly limited, for example. The adjustment may be performed by adding an alkaline regent to the sample, for example. Examples of the alkaline reagent include an alkali, an aqueous alkali solution, and a buffer solution under the alkaline conditions as mentioned above.

In the case where the insoluble pH conditions are neutral conditions, a method for adjusting the sample to be under neutral conditions is not particularly limited, for example. The adjustment may be performed by adding an acidic reagent, an alkaline reagent, or a neutral reagent according to the original pH conditions of the sample, for example. Examples of the neutral reagent include water, an aqueous neutral solution, and a buffer solution under the neutral conditions as mentioned above.

In (y), for example, a mixture under the insoluble pH conditions can be prepared by mixing a sample and a chelating agent adjusted to be under the insoluble pH conditions, and in the mixture, a complex can be formed. At that time, for example, the pH of the chelating agent is adjusted so that the mixture prepared by mixing with the sample is under the insoluble pH conditions.

A method for adjusting the chelating agent to be under the insoluble pH conditions is not particularly limited. As a specific example, a dispersion liquid of the chelating agent, adjusted to be under the insoluble pH conditions, can be obtained by dispersing the chelating agent in the dry state in a non-organic medium in which the chelating agent is not dissolved. As the non-organic medium in which the chelating agent is dispersed, the above-mentioned dispersion medium can be used, and the non-organic medium is the same as the acidic reagent, the alkaline reagent, the neutral reagent, or the like.

Since the chelating agent in the dry state is superior in dispersibility in a non-organic medium, for example, the chelating agent is preferably a freeze-dried chelating agent or a dried chelating agent under reduced pressure. A method for producing these dried chelating agents is not particularly limited, and they can be obtained by mixing the chelating agent in an organic medium and thereafter subjecting the mixture to freeze drying or drying under reduced pressure. The organic medium is not particularly limited, and t-butyl alcohol, 2-propanol, or the like can be used, for example.

In (z), for example, a mixture under the insoluble pH conditions can be prepared by mixing a non-organic medium under the insoluble pH conditions, a chelating agent, and a sample, and in the mixture, a complex can be formed. At that time, for example, the pH of the non-organic medium is adjusted so that the mixture prepared by mixing with the chelating agent and the sample is under the insoluble pH conditions.

As the non-organic medium under the insoluble pH conditions, any of the above-mentioned acidic reagents, alkaline reagents, and neutral reagents can be used as mentioned above, for example.

A method for mixing the chelating agent and the sample is not particularly limited, and examples thereof include conventional methods such as mixing thoroughly, mixing by vibration, and mixing by ultrasound.

In the present embodiment, the mixture may further contain a masking agent in addition to the chelating agent and the sample. The masking agent may be mixed, in advance, with a sample, a chelating agent, a non-organic medium, or an inorganic salt. The masking agent may be mixed with any of the sample and the chelating agent before or after adjusting to be under the insoluble pH conditions or mixed after mixing the inorganic salt, the sample, and the chelating agent.

In the present embodiment, the mixture may further contain other components. The other components are not particularly limited, and examples thereof include an oxidizing agent and a reducing agent. The oxidizing agent can be used to improve the reactivity of a reaction of forming a complex between the chelating agent and the metal, for example. The reducing agent can be used to cancel an excess amount of the oxidizing agent in the case where the mixture contains an excess amount of the oxidizing agent, for example.

The process conditions in the complex formation are not particularly limited, and the process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, and preferably from 30 seconds to 30 minutes.

As mentioned above, the mixture may contain an inorganic salt in advance, or an inorganic salt may be mixed after the process of the complex formation before the subsequent complex recovering step, for example.

In the former case, for example, in (x) to (z), the inorganic salt may be mixed, in advance, with the sample, the chelating agent, or the non-organic medium. The inorganic salt may be mixed with any of the sample and the chelating agent before or after adjusting to be under the insoluble pH conditions. In the latter case, for example, the inorganic salt may be mixed with the mixture after the complex formation.

The form of the inorganic salt is not particularly limited and may be, for example, in the dry state (or also referred to as the solid state) or the liquid state. In the latter case, a solvent of the inorganic salt is not particularly limited and can be, for example, a non-organic medium.

(1B) Complex Recovering Step

The complex recovering step is a step of filtrating the mixture in the presence of an inorganic salt, thereby recovering the complex. The conditions of mixing the inorganic salt with the mixture are, for example, as mentioned above as long as the inorganic salt is present together in the mixture in filtration.

As mentioned above, the chelating agent can maintain the state of not being dissolved under the insoluble pH conditions. Therefore, a complex between the chelating agent and the metal is present also in the state of not being dissolved. Therefore, in this complex recovering step, the undissolved complex present in the mixture is recovered by filtration.

A method for the filtration is not particularly limited as long as a filter medium is used, for example, and after the filtration, a residue on the filter medium can be recovered as the complex. Examples of the method for the filtration include natural filtration, filtration under reduced pressure, pressure filtration, and centrifugal filtration, using a filter medium. The filter medium for use in the filtration is not particularly limited and can be, for example, any of the above-mentioned filters. The conditions of the filtration process are not particularly limited and can be set appropriately according to the kind of the filter medium and the like, for example.

In the present embodiment, as mentioned above, the complex recovered in the complex recovering step may be regarded as the metal, the complex solution obtained by dissolving the complex in the optional complex dissolving step mentioned below may be regarded as the metal, or the metal may be isolated by removing the chelating agent from the complex in the optional metal isolating step mentioned below.

(1C) Complex Dissolving Step

The complex dissolving step is a step of dissolving the recovered complex in an aqueous medium under alkaline conditions.

The chelating agent is dissolved under alkaline conditions. Therefore, by mixing the recovered complex in an aqueous medium under alkaline conditions, the chelating agent can be dissolved in the complex state in an aqueous medium. The aqueous medium in which the complex is dissolved is also referred to as an aqueous complex solution. Although it is preferred that the complex is completely dissolved in an aqueous medium, the complex may partially remain in the insoluble state. The complex in the insoluble state is, for example, preferably a detection limit or less.

In the complex dissolving step, the alkaline conditions are not particularly limited, and the lower limit thereof is, for example, preferably pH 9, more preferably pH 11. The upper limit thereof is not particularly limited and is, for example, preferably pH 12. The alkaline conditions can be set appropriately according to the kind of the chelating agent used. In the case where the insoluble pH conditions in the complex forming step are alkaline conditions, the alkaline conditions in the complex dissolving step are preferably higher than the former pH.

A method for dissolving the complex is not particularly limited. For example, the complex may be dissolved by adding an aqueous medium adjusted to be under alkaline conditions in advance to the complex or by adding an aqueous medium to the complex and thereafter adjusting the mixture to be under alkaline conditions.

A method for adjusting to be under alkaline conditions is not particularly limited, and the alkaline reagent can be used, for example. Examples of the alkaline reagent include an alkali, an aqueous alkali solution, and a buffer solution under alkaline conditions. The alkali is not particularly limited, and examples thereof include sodium hydroxide and potassium hydroxide. Examples of the aqueous alkali solution include solutions obtained by diluting an alkali with water or a buffer solution. The buffer solution for use in the dilution of the alkali is not particularly limited, and any of the above-mentioned common buffer solutions can be used. The concentration of alkali in the aqueous alkali solution is not particularly limited and is, for example, from 0.1N to 1N. The buffer solution under alkaline conditions is not particularly limited, and examples thereof include Tris-NaOH, Tris-HCl, a carbonate buffer, and Good's buffers. The concentration of the buffer solution is not particularly limited and is, for example, from 10 to 100 mmol/L.

A method for mixing the complex and the aqueous medium is not particularly limited, and examples thereof include conventional methods such as mixing thoroughly, mixing by vibration, and mixing by ultrasound.

The amount of the aqueous medium to be added relative to the complex is not particularly limited. The amount of the aqueous medium to be added is, for example, preferably an amount in which the recovered complex can be dissolved. The amount of the aqueous medium to be added is, for example, preferably an amount smaller than the liquid amount of the sample. Therefore, for example, a metal-containing liquid with a concentration higher than the sample used can be obtained. That is, a metal-containing liquid in which a metal is concentrated compared with the sample can be obtained. The amount of the aqueous medium to be added is, for example, in the range from $\frac{1}{2}$ to $\frac{1}{100}$, preferably from $\frac{1}{10}$ to $\frac{1}{50}$, and more preferably $\frac{1}{50}$ relative to the liquid amount of the sample.

(1D) Metal Isolating Step

The metal isolating step is a step of isolating the metal from the complex. The complex recovered in the step (1B) or the complex dissolved in the aqueous medium in the step (1C) may be subjected to the metal isolating step, for example.

In the metal isolating step, the metal as a single metal can be recovered from the complex by decomposing the chelating agent in the complex. A method for decomposing the chelating agent is not particularly limited and can be, for example, a known method such as ashing. Examples of the ashing include wet ashing and dry ashing. The wet ashing can be performed according to the Mercury Analysis Manual (Ministry of the Environment, March 2004), for example.

The present embodiment is described below with reference to an example of the method where the insoluble pH conditions are acidic conditions, dithizone is used as the chelating agent, an urine sample is used as the sample, and a complex between mercury as the metal and the dithizone is recovered by filtration with a filter in the presence of an inorganic salt. This, however, is merely an example and does not limit the present invention.

First, an urine sample is prepared. The amount of the sample is not particularly limited and is, for example, in the range from 1 to 100 mL, preferably from 1 to 20 mL, more preferably from 5 to 10 mL.

The pH of the sample is then adjusted to be under acidic conditions by adding an acidic reagent. The amount of the acidic reagent to be added is not particularly limited and is, for example, in the range from 1 to 10 μL relative to 1 mL of the sample. The acidic reagent is, for example, preferably an aqueous hydrochloric acid solution, and the normality thereof is, for example, in the range from 1N to 8N.

Freeze-dried dithizone is added to a tube, and the sample after the pH adjustment is added thereto. The amount of dithizone is, for example, from 0.1 to 0.3 mg, preferably 0.3 mg relative to 1 mL of the sample. At that time, the pH of the mixture containing the dithizone added is, for example, from 1 to 4, preferably from 1 to 2.

The prepared mixture is left as is for a predetermined time to from a complex between the dithizone and mercury in the urine sample. The process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

The inorganic salt is mixed in the sample after the complex formation, which is then left standing for a predetermined time. The concentration of the inorganic salt in the mixture containing the inorganic salt mixed therein is as mentioned above. The process temperature is, for example, 24° C., and the process time is, for example, from 1 to 10 minutes. As mentioned above, the inorganic salt may be mixed in the mixture before the complex formation.

Subsequently, the mixture is filtered with a filter in the presence of the inorganic salt, and a residue on the filter is recovered as the complex. The filter is, for example, as mentioned above.

It is preferred that the filter is used by arranging inside a cylindrical body such as column, for example. In this case, the mixture can be filtered by adding the mixture on the upper surface of the filter from the upper side in the axis direction of the cylindrical body. A method for the filtration is not particularly limited, is as mentioned above, and is, for example, preferably natural filtration. The sizes of the filter and the column are not particularly limited and can be determined appropriately according to the amount of the mixture to be subjected to the filtration and the like, for example. In the present embodiment, the filter medium is, for example, preferably a filter with a pore(s) in the range from 1 to 90 μm and can be, for example, specifically a glass fiber filter paper with the pore(s).

The metal can be recovered as the complex as described above. In the present embodiment, as mentioned above, the metal may be isolated from the recovered complex.

When the metal is isolated from the recovered complex, an alkaline reagent is added to the recovered complex to dissolve the complex in the alkaline reagent.

The amount of the alkaline reagent to be added is not particularly limited and is, for example, in the range from 10 to 200 μL, preferably from 20 to 100 μL, more preferably 20 μL relative to 1 mL of the urine sample. The pH of the alkaline reagent is, for example, from 9 to 12, preferably from 11 to 12. The alkaline reagent is, for example, preferably an aqueous sodium hydroxide solution, and the normality thereof is, for example, in the range from 0.1N to 1N, preferably 0.4N.

Accordingly, mercury in the complex state, dissolved in the aqueous solvent, can be recovered. Moreover, for example, by subjecting the complex to wet ashing, the dithizone in the complex can be decomposed, and only mercury can be recovered.

(2) Second Embodiment

The metal recovery method of the second embodiment shows an example where chelating agents represented by the following structural formulae (4) and (5) are used as the chelating agent, the mixture is filtrated in the presence of an inorganic salt to recover a first complex between the chelating agent represented by the structural formula (4) and the metal, and the metal derived from the first complex are recovered in an aqueous medium containing the chelating agent represented by the structural formula (5). The present embodiment can be described with reference to the description of the first embodiment unless otherwise shown.

In the present embodiment, the chelating agent represented by the following structural formula (4) is referred to as the first chelating agent, and the chelating agent represented by the following structural formula (5) is referred to as the second chelating agent.

(5)

The second chelating agent represented by the structural formula (5) is meso-2,3-dimercapto succinic acid (DMSA). Hereinafter, the second chelating agent is also referred to as DMSA.

In the metal recovery method of the present embodiment, the complex forming step includes the following step (2A), and the metal recovering step includes the following step (2B) and optionally includes the following steps (2C), (2D), and (2E).

(2A) a first complex forming step of preparing a mixture of a sample and a first chelating agent under pH conditions where the chelating agent is insoluble in an aqueous medium to form a first complex between a metal in the sample and the first chelating agent in the mixture;

(2B) a first complex recovering step of filtrating the mixture in the presence of an inorganic salt, thereby recovering the first complex;

(2C) a second complex forming step of preparing a mixture of the first complex and an aqueous second chelating agent solution under pH conditions where the first chelating agent is insoluble in the aqueous second chelating agent solution to form a second complex between the metal derived from the first complex and the second chelating agent in the mixture;

(2D) a second complex recovery step of recovering a liquid fraction containing the second complex dissolved therein from the mixture to recover the metal;

(2E) a metal isolating step of isolating the metal from the second complex.

(2A) First Complex Forming Step

The first complex forming step is a step of preparing a mixture of a first chelating agent and a sample to form a first complex between the first chelating agent and a metal in the sample in the mixture. In the first complex forming step, the mixture is prepared under pH conditions where the first chelating agent is insoluble in an aqueous medium. Hereinafter, the pH conditions where the first chelating agent is insoluble in an aqueous medium is also referred to as the "first pH conditions". The first pH conditions are the "insoluble pH conditions" in the first embodiment and can be described with reference to the description of the first embodiment.

The first complex forming step (2A) is the step (1A) in the first embodiment and can be described with reference to the description of the first embodiment.

(2B) First Complex Recovering Step

The first complex recovering step is a step of filtrating the mixture obtained in the first complex forming step in the presence of an inorganic salt, thereby recovering the first complex.

The first complex forming step (2B) is the step (1B) in the first embodiment and can be described with reference to the description of the first embodiment.

The first complex recovered in the first complex recovering step as described above may be regarded as the metal. The mixture of the first complex and the aqueous second chelating agent solution, prepared in the optional second complex forming step described below, or the liquid fraction containing the second complex dissolved therein in the optional second complex recovering step described below may be regarded as the metal. The metal may be isolated by removing the first chelating agent and the second chelating agent from the mixture prepared in the second complex forming step or by removing the second chelating agent in the second complex from the liquid fraction in the second complex recovering step.

(2C) Second Complex Forming Step

The second complex forming step is a step of preparing a mixture of the first complex and an aqueous second chelating agent solution to form a second complex between the metal derived from the first complex and the second chelating agent in the mixture. In the second complex forming step, the aqueous second chelating agent solution is under pH conditions where the first chelating agent is insoluble. Hereinafter, the "pH conditions where the first chelating agent is insoluble" are also referred to as the "second pH conditions".

In the mixture, the second chelating agent is in a state of being dissolved, and the first complex can maintain the state of not being dissolved. When the first complex and the second chelating agent are present in the mixture, all or a part of the metal forming the first complex is dissociated from the first complex and is bound to the second chelating agent, thereby forming a second complex between the second chelating agent and the metal, although the mechanism is unknown.

The second pH conditions are, for example, pH conditions where the second chelating agent is soluble in an aqueous medium, and the first chelating agent is insoluble in an aqueous medium. In the second complex forming step, the pH conditions of the aqueous second chelating agent solution and the pH conditions of the mixture of the aqueous solution and the first complex are preferably the second pH conditions.

The second pH conditions can be, for example, non-alkaline conditions, and specific examples thereof include acidic conditions (pH 2 to pH 3), mildly acidic conditions (pH 4 to pH 5), and neutral conditions (pH 6 to pH 7). The upper limit of the second pH conditions is not particularly limited and is, for example, pH 6.8, preferably pH 6, and more preferably pH 4. The lower limit of the second pH conditions is not particularly limited and is, for example, pH 2, preferably pH 3, and more preferably pH 4. The second pH conditions can be set appropriately according to the kinds of the first chelating agent and the second chelating agent and the like, for example.

The aqueous second chelating agent solution is not limited as long as the second chelating agent is dissolved in an aqueous medium, for example. Although it is preferred that the second chelating agent is in a state of being completely dissolved in the aqueous solution, the second chelating agent may be in a state of being partially dissolved. In the latter case, the second chelating agent is not limited as long as an amount in which a complex with a metal derived from the first complex can be formed is present in the aqueous solution, for example.

The aqueous second chelating agent solution may be prepared by adjusting an aqueous medium to be under the second pH conditions and thereafter dissolving a second chelating agent therein or by adding a second chelating agent to an aqueous medium and thereafter adjusting the pH of this mixture thus obtained to be under the second pH conditions to dissolve the second chelating agent, for example.

In the former case, since DMSA as the second chelating agent is a strong acid, it is preferred that the aqueous medium in which the second chelating agent is dissolved is, for example, an alkaline reagent. By dissolving the second chelating agent in an alkaline reagent, an aqueous solution under the second pH conditions, preferably non-alkaline conditions can be prepared. The pH of the alkaline reagent is not particularly limited, the lower limit thereof is, for example, 8, preferably 9, and more preferably 10, and the upper limit thereof is, for example, 12, preferably 11. The alkaline reagent is not particularly limited and is, for example, preferably an aqueous alkaline solution, more preferably an alkaline buffer solution. The aqueous alkaline solution can be, for example, an aqueous trisodium phosphate solution. Examples of the alkaline buffer solution include a phosphate buffer solution, a tris buffer solution, and Good's buffers. The concentrations of the aqueous solution and the buffer solution are not particularly limited and are, for example, from 10 to 100 mmol/L, preferably 100 mmol/L.

In the latter case, the aqueous medium is not particularly limited, and any of water, an aqueous solution, a buffer solution, and the like can be used, for example. For example, the pH adjustment to be under the second pH conditions may be performed after mixing the aqueous medium and the second chelating agent, for example. The method for the adjustment is not particularly limited, and any of an acidic reagent, an alkaline reagent, a neutral reagent, and the like can be used appropriately.

The concentration of the second chelating agent in the aqueous second chelating agent solution is not particularly limited and is, for example, from 5 to 20 mg/mL, preferably from 10 to 20 mg/mL.

A method for mixing the first complex and the aqueous second chelating agent solution is not particularly limited, and examples thereof include conventional methods such as mixing thoroughly, mixing by vibration, and mixing by ultrasound.

In the mixture, the amount of the aqueous second chelating agent solution to be added is not particularly limited and is, for example, from 10 to 200 µL, preferably from 20 to 100 µL, and more preferably 20 µL relative to 1 mL of the sample used in the first complex forming step. In the mixture, the ratio between the first complex and the second chelating agent to be added is not particularly limited. The ratio (weight ratio) between the first chelating agent used in the first complex forming step and the second chelating agent used in the second complex forming step is, for example, from 1:0.3 to 1:40, preferably from 1:7 to 1:40, and more preferably from 1:10 to 1:40.

The amount of the aqueous second chelating agent solution to be added relative to the first complex is not particularly limited. The amount of the aqueous second chelating agent solution to be added is, for example, preferably smaller than the liquid amount of the sample used. With this amount, for example, a metal-containing liquid with a concentration higher than the sample used can be obtained. That is, a metal-containing liquid in which a metal is concentrated compared with the sample can be obtained. The amount of the aqueous second chelating agent solution to be added is, for example, in the range from ½ to 1/100, preferably from 1/10 to 1/50, and more preferably 1/50 relative to the liquid amount of the sample.

The mixture may further contain other components in addition to the first complex and the aqueous second chelating agent solution. The other components are not particularly limited, and examples thereof include an oxidizing agent and a reducing agent as mentioned above.

The process conditions of the second complex formation are not particularly limited, and the process temperature is, for example, room temperature, and the process time is, for example, from 30 seconds to 10 minutes.

(2D) Second Complex Recovering Step

The second complex recovering step is a step of recovering a liquid fraction containing the second complex dissolved therein, formed in the second complex forming step, from the mixture, thereby recovering the metal.

As mentioned above, since the second chelating agent under the second pH conditions is in a state of being dissolved in the mixture, the second complex between the second chelating agent and the metal is present also in a state of being dissolved in the mixture. On the other hand, since the first chelating agent is in the insoluble state in the mixture, it is present in the state of not being dissolved in the mixture. Then, the liquid fraction containing the second complex dissolved therein is recovered in this second complex recovering step, thereby recovering the metal. Although it is preferred that the second complex is completely dissolved in the mixture, the second complex may partially be in the state of not being dissolved. The amount of the undissolved second complex is, for example, preferably a detection limit or less.

A method for recovering the complex is not particularly limited, and for example, a known method for separating a solid and a liquid can be employed. Examples of the recovering method include processes such as filtration, centrifugal separation, precipitation, membrane separation, adsorption, and freeze-drying. The process conditions of the recovery are not particularly limited and can be set appropriately according to the kind and the amount of the complex, for example. For example, in the case of the filtration using a filter medium, a fraction passed through the filter medium can be recovered as a liquid fraction after the filtration.

In the present embodiment, the metal recovering step may further include a chelate decomposing step of decomposing the second chelating agent in the second complex after the recovery of the liquid fraction. By decomposing the second chelating agent as described above, a metal as a single metal can be recovered from the second complex. A method for decomposing the second chelating agent is not particularly limited and can be, for example, a known method such as ashing and can be described with reference to the description of the first embodiment.

The present embodiment is described below with reference to an example of the method where the first pH conditions are acidic conditions, the second pH conditions are mildly acidic to neutral conditions, dithizone is used as the first chelating agent, DMSA is used as the second chelating agent, an urine sample is used as the sample, and a first complex between mercury as the metal and the dithizone is performed by filtration with a filter in the presence of an inorganic salt. This, however, is merely an example and does not limit the present invention.

In the same manner as in the first embodiment, the pH of the urine sample is adjusted, the dithizone is added to the sample after the pH adjustment, and a complex between the dithizone and mercury in the sample is formed.

Then, in the same manner as in the first embodiment, the mixture is filtrated using a filter in the presence of an inorganic salt to recover the residue on the filter as the first complex.

Subsequently, the recovered first complex and the aqueous DMSA solution are mixed. Accordingly, a second complex is formed in the mixture of the first complex and the aqueous DMSA solution.

The aqueous DMSA solution can be prepared by dissolving DMSA in an aqueous alkaline solution. The aqueous alkaline solution is, for example, preferably an aqueous trisodium phosphate solution, the concentration thereof is, for example, from 10 to 100 mmol/L, and the pH thereof is, for example, from 9 to 12. The concentration of DMSA in the aqueous DMSA solution is, for example, from 5 to 20 mg/mL. The pH of the DMSA solution is, for example, in the range from 2 to 6, preferably from 4 to 6, more preferably 4.

The amount of the aqueous DMSA solution to be added relative to the first complex is not particularly limited and is, for example, in the range from 10 to 200 µL, preferably from 20 to 100 µL, and more preferably 20 µL relative to 1 mL of the urine sample. The pH of the mixture of the first complex and the DMSA solution is, for example, in the range from 2 to 6, preferably from 4 to 6, and more preferably 4.

Subsequently, the mixture is subjected to centrifugal separation to separate a supernatant containing the second complex dissolved therein and a precipitation, thereby recovering the supernatant.

As described above, mercury dissolved in the liquid fraction in the second complex state can be recovered. By subjecting the second complex to wet ashing or the like, DMSA in the second complex is decomposed, thereby recovering only mercury. Although the recovery of mercury is described above as an example, the present invention is not limited thereto.

(3) Third Embodiment

The first embodiment shows an example where a chelating agent represented by the following structural formula (6) is used as the second chelating agent, and a metal is recovered using an aqueous medium. The present embodiment can be described with reference to the description of the second embodiment unless otherwise shown.

(6)

In the structural formula (6), $R^3$ represents an alkyl group or an amino alkyl group each with a carbon number of 1 or 2 or is not present, and Y represents Examples of the second chelating agent include tiopronin (N-(2-mercaptopropionyl)glycine) represented by the following structural formula (6-1), DMPS (2,3-dimercapto-1-propanesulfonic acid sodium salt) represented by the following structural formula (6-2), and cysteine (2-amino-3-sulfanyl propanoic acid) represented by the following structural formula (6-3). The second chelating agent may be, for example, any of hydrates of compounds having the structural formula (6). The second chelating agent may be, for example, any of tautomers and stereoisomers thereof. Examples of the isomers include geometric isomers and conformers. As the second chelating agent, a commercially available product may be used, for example. The tiopronin is available from KANTO CHEMICAL CO., INC., Tokyo Chemical Industry Co., Ltd., Wako Pure Chemical Industries, Ltd., or the like, for example. The DMPS is available from Wako Pure Chemical Industries, Ltd. or the like, for example. The cysteine is available from NACALAI TESQUE, INC. or the like, for example. The second chelating agents may be used alone or in a combination of two or more of them.

(6-1)

The metal recovery method of the present embodiment can be described with reference to the description of the second embodiment unless otherwise shown except that the second chelating agent represented by the structural formula (6) is used and is specifically performed in the same manner as in the steps (2A) to (2E).

In the second complex forming step (2C), a mixture of a first complex and an aqueous second chelating agent solution is prepared to form a second complex between a metal derived from the first complex and the second chelating agent in the mixture.

In the step (2C), the second pH conditions are, for example, pH conditions where the second chelating agent is soluble in an aqueous medium, and the first complex is insoluble in an aqueous medium. In the second complex forming step, the pH conditions of the aqueous second chelating agent solution and the pH conditions of the mixture of the aqueous solution and the first complex are preferably the second pH conditions. The pH of the mixture is not limited as long as the first chelating agent is not dissolved in the mixture.

The second pH conditions can be, for example, non-alkaline conditions, and specific examples thereof include acidic conditions (pH 1 to pH 3), mildly acidic conditions (pH 4 to pH 5), and neutral conditions (pH 6 to pH 7). The upper limit of the second pH conditions is not particularly limited and is, for example, pH 6.8, preferably pH 6, and more preferably pH 4. The lower limit of the second pH conditions is not particularly limited and is, for example, pH 4, preferably pH 3, and more preferably pH 2, yet more preferably pH 1. The second pH conditions can be set appropriately according to the types of the first chelating agent and the second chelating agent and the like, for example.

The aqueous second chelating agent solution is not limited as long as the second chelating agent is dissolved in an aqueous medium, for example. Although it is preferred that the second chelating agent is in a state of being completely dissolved in the aqueous solution, the second chelating agent may be in a state of being partially dissolved, for example. In the latter case, it is only necessary that the amount of the remaining second chelating agent being present in the aqueous solution is the amount capable of forming a complex with the metal derived from the first complex in a state of being dissoleved.

The aqueous second chelating agent solution may be prepared by adjusting an aqueous medium to be under the second pH conditions and thereafter dissolving a second chelating agent or by adding a second cheating agent to an aqueous medium and thereafter adjusting the pH of the mixture thus obtained to be under the second pH conditions, for example.

In the former case, the aqueous medium in which the second chelating agent is dissolved is not particularly limited, and for example, water, an aqueous solution, a buffer solution, or the like can be used. The aqueous medium is adjusted to be under the second pH conditions, and the second chelating agent is thereafter dissolved, for example. The method for the adjustment is not particularly limited, and for example, an acidic reagent, an alkaline reagent, a neutral reagent, and the like can be used appropriately, for example.

In the latter case, the aqueous medium is not particularly limited, and for example, water, an aqueous solution, a buffer solution, or the like can be used. The aqueous medium and the second chelating agent are mixed, and the mixture is thereafter adjusted to be under the second pH conditions, for example. The method for the adjustment is not particularly limited, and for example, an acidic reagent, an alkaline reagent, a neutral reagent, and the like can be used appropriately, for example.

The concentration of the second chelating agent in the aqueous second chelating agent solution is not particularly limited and is, for example, from 15 to 300 mg/mL, preferably from 75 to 150 mg/mL. In the present embodiment, the second chelating agent is preferably any of tiopronin, DMPS, and cysteine because they are particularly superior in solubility, for example. For example, as the concentration of the second chelating agent in the aqueous second chelating agent solution is increased, the amount of the formed second complex between the metal derived from the first complex and the second chelating agent is increased. Thus, the metal recovery yield can be further improved.

The present embodiment is described below with reference to an example of the method where the first pH conditions are acidic conditions, the second pH conditions are mildly acidic to neutral conditions, dithizone is used as the first chelating agent, DMPS is used as the second chelating agent, an urine sample is used as the sample, and a first complex between mercury as the metal and the dithizone is recovered by filtration with a filter in the presence of an inorganic salt. This, however, is merely an example and does not limit the present invention.

In the same manner as in the first embodiment, a masking agent is added to the urine sample, the pH of the mixture thus obtained is adjusted, the dithizone is added to the mixture after the pH adjustment, and a complex between the dithizone and mercury in the sample is formed.

Then, in the same manner as in the first embodiment, the mixture is filtrated with a filter in the presence of an inorganic salt, and a residue on the filter is recovered as a first complex.

Subsequently, the recovered first complex and an aqueous DMPS solution are mixed to form a second complex in the mixture of the first complex and the aqueous DMPS solution.

The aqueous DMPS solution can be prepared by dissolving DMPS in a medium. Examples of the medium include an aqueous trisodium phosphate solution, nitric acid, acetic acid, phosphoric acid, citric acid, a phosphate buffer solution, and a tris buffer solution. The concentration of the medium is, for example, from 10 to 100 mmol/L. The pH of the medium is not particularly limited as long as the pH is in the range in which dithizone is not dissolved. The concentration of DMPS in the aqueous DMPS solution is, for example, from 5 to 20 mg/mL. The pH of the DMPS solution is, for example, in the range from 2 to 6, preferably from 4 to 6, more preferably 4.

The amount of the aqueous DMPS solution to be added relative to the first complex is not particularly limited and is, for example, in the range from 10 to 200 µL, preferably from 20 to 100 µL, more preferably 20 µL relative to 1 mL of the urine sample. The pH of the mixture of the first complex and the aqueous DMPS solution is, for example, in the range from 1 to 6, preferably from 1 to 3, and more preferably 1.

Subsequently, the mixture is subjected to centrifugal separation to separate a supernatant containing the second complex dissolved therein and a precipitation, thereby recovering the supernatant.

As described above, mercury dissolved in the liquid fraction in the second complex state can be recovered. By subjecting the second complex to wet ashing or the like, DMPS in the second complex is decomposed, thereby recovering only mercury, for example. Although the recovery of mercury is described above as an example, the present invention is not limited thereto. Moreover, although the present embodiment shows an example in the case where DMPS is used as the second chelating agent, a metal can be recovered in the same manner as in the present embodiment also in the case where tiopronin, cysteine, or the like is used as the second chelating agent, for example.

(4) Other Embodiments

In the metal recovery method of the present invention, the optional metal isolating step may be, for example, a method for extracting the complex with an organic solvent besides the recovery using an aqueous medium in the embodiments. In this case, for example, the metal isolating step may be performed according to a dithizone method (colorimetric method) or an atomic absorption method, defined in JIS K0101 or K0102.

<Method for Analyzing Metal>

As mentioned above, the method for analyzing a metal of the present invention includes: a metal recovering step of recovering a metal from a sample by the metal recovery method of the present invention; and an analyzing step of analyzing the metal. The method for analyzing a metal of the present invention is characterized in that it includes the metal recovering step of recovering a metal from a sample by the metal recovery method of the present invention, and the other steps and conditions are not limited. The metal recovering step can be performed with reference to the metal recovery method of the present invention.

The analyzing step is not particularly limited and can be selected appropriately according to the kind of the metal to be analyzed, for example. The analysis of the metal can be performed by, for example, an optical measurement, GC-ECD (gas chromatography-electron capture detector), an electrochemical measurement (e.g., stripping voltammetry), or the like. The analysis by optical measurement can be performed by measuring an absorbance, a transmittance, a reflectance, or the like using an optical analyzer or the like, for example. Examples of the optical analyzer include an atomic absorption spectrometer and a visible spectrometer. The analysis of the metal may be qualitative analysis or quantitative analysis, for example.

The method for analyzing a metal of the present invention may further include a step of correcting a measurement value, for example. In the step of correcting a measurement value, a measurement value as a measurement result can be corrected according to the correlation between the measurement value and the metal concentration in a sample, for example. The correlation can be obtained as follows, for example. A metal in the standard samples with the known metal concentrations is recovered by the metal recovery method of the present invention, and measurement values of the metal and the corresponding metal concentrations of the standard samples are plotted. It is preferred that the standard samples are in a dilution series of the metal. By correcting measurement values as described above, it becomes possible to perform the quantitative determination with higher reliability.

The metal as the above-mentioned complex may be analyzed, or the metal as a single metal obtained by isolating the metal from the complex may be analyzed, for example. In the latter case, it is preferred that the metal recovering step includes, as mentioned above, the step of decomposing the chelating agent in the complex, i.e., the step of isolating the metal from the complex.

<Metal Recovery Reagent>

As mentioned above, the metal recovery reagent of the present invention is for use in the metal recovery method of the present invention and contains: a chelating agent for metal; and an inorganic salt. The metal recovery reagent of the present invention is characterized in that it contains a chelating agent and an inorganic salt, and the other configurations and conditions are not particularly limited. The chelating agent and the inorganic salt can be described with reference to the description of the metal recovery method of the present invention, for example.

In the metal recovery reagent of the present invention, the chelating agent and the inorganic salt may be contained in different containers or the same container with or without mixing, for example. In the case where the chelating agent and the inorganic salt are contained in different containers, the metal recovery reagent of the present invention is also referred to as a metal recovery kit.

The metal recovery reagent of the present invention may further contain at least one of the masking agent and the other reagents in addition to the chelating agent and the inorganic salt. The other reagents are not particularly limited, and examples thereof include the above-mentioned oxidizing agent and reducing agent. The masking agent, the oxidizing agent, and the reducing agent are not particularly limited, and examples of them in the metal recovery method of the present invention can be used, for example. The other reagents may be contained in a container different from the container for the chelating agent or the inorganic salt or in the same container as either one of the container(s) for the chelating agent and the inorganic salt with or without mixing, for example.

EXAMPLES

The examples of the present invention are described below. The present invention, however, is not limited by the following examples.

Example 1

It was demonstrated that the recovery yield of a complex between dithizone and a metal was improved by adding various inorganic salts.

(1-1) Observation of complex recovery leakage by visual observation of filtrate

N-methyl maleimide was added to 1 mL of an urine sample so as to have a concentration of 12.5 mol/L, which was then stood still at 24° C. for 15 minutes. 0.1 mL of 1 mol/L citric acid-sodium citrate buffer solution (pH 2.0) was added to the sample after being stood still to adjust the pH of the sample to be an acidic pH. Subsequently, 10 µL of 0.1 mol/L aqueous sodium hydroxide solution containing 4 mmol/L dithizone (hereinafter referred to as a dithizone reagent) was added to the sample after the pH adjustment to prepare a mixture. The mixture was then shaken at 24° C. for 20 minutes using a shaker. Thus, a complex was formed. Furthermore, an inorganic salt was added to the mixture after the complex formation so as to have a concentration shown in Table 2 below, which was then stood still at 24° C. for 5 minutes.

The mixture after being stood still was then subjected to centrifugal filtration at 300×g for 5 minutes using a column including filters arranged therein and having a diameter of 7.5 cm. As the filters, three kinds of glass fiber filter paper shown in Table 1 below were used, and four layers of F1, F2, F3, and F4 were arranged in the direction of an axis of the column. The filters are arranged in order of decreasing the pore (pore size) from the mixture introduction side to the mixture discharge side in the column, i.e., in the direction from upward to downward in the column.

TABLE 1

| Filter | Pore size |
| --- | --- |
| F1 | 23 µm |
| F2 | |
| F3 | 2.7 µm * |
| F4 | 1 µm * |

* Particle retention capacity

Then, the obtained filtrate was centrifuged at 15,000 rpm for 5 minutes to separate a precipitate containing the complex and a supernatant. The precipitate was subjected to visual observation to observe coloring in blue derived from the dithizone. When coloring of the precipitate in blue was observed, it was determined that the complex passed through the filters and a complex recovery leakage was generated (+), and when coloring of the precipitate in blue was not observed, it was determined that the complex was trapped on any of the filters, and a complex recovery leakage was not generated (−). As a control, visual observation was performed in the same manner as described above except that an inorganic salt was not added.

The results of these are shown in Table 2. As shown in Table 2, the complex recovery leakage was generated in the control (non-addition of inorganic salt), whereas the complex recovery leakage was not observed at all of the concentrations of the inorganic salt in the case where each of the inorganic salts of KCl, $Na_2SO_4$, and $MgCl_2 \cdot 6H_2O$ was added. It was demonstrated that the recovery leakage caused by the complex passing through the filters could be prevented by causing the inorganic salt to be present together in the mixture of the metal and the chelating agent.

TABLE 2

| Inorganic salt | Concentration | The presence or absence of complex recovery leakage |
| --- | --- | --- |
| Non-addition | None | + |
| KCl | 1 mol/L | − |
| | 2 mol/L | − |
| $Na_2SO_4$ | 2 mol/L | − |
| | 3 mol/L | − |
| $MgCl_2 \cdot 6H_2O$ | 1 mol/L | − |
| | 2 mol/L | − |
| | 3 mol/L | − |

+: The presence of recovery leakage
−: The absence of recovery leakage (1-2) Observation of Complex Recovery by Visual Observation of Filters The filters were collected from the column used in (1-1). The surfaces of the filters on the mixture introduction side were subjected to visual observation to observe whether the complex was trapped on which filter. Since the four layers of the filters were used as mentioned above, when the entire complex was trapped on any of the filters, there is no complex to be trapped on the filter arranged on the mixture discharge side from the filter on which the complex is trapped, and thus, the filter arranged on the mixture discharge side is white.

Figure 1:
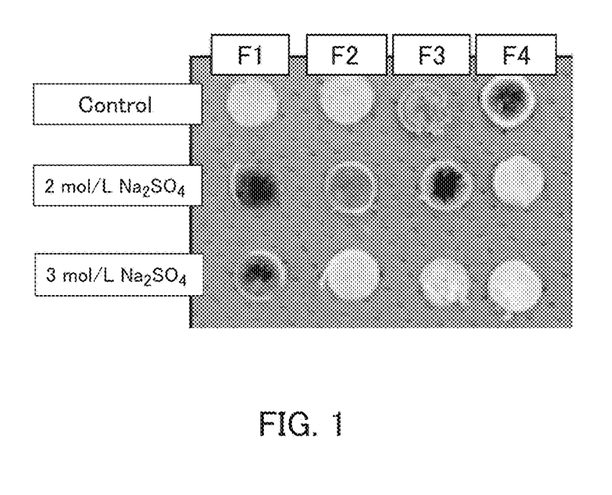
FIG. 1 is a photograph showing each filter after filtration in Example 1.

The results of these are shown in FIG. 1. FIG. 1 is a photograph obtained by taking the surfaces of the filters on the mixture introduction side. In FIG. 1, the left side of the photograph indicates the kind and the concentration of the inorganic salt, and the upper side of the photograph indicates the kind of each filter. In FIG. 1, the filters are arranged in order from the mixture introduction side to the mixture discharge side from the left side to the right side of the photograph. As shown in FIG. 1, as to the control, coloring of F1 and F2 (the same kind of filter) with large pore sizes was not observed, slight coloring of F3 with a smaller pore size was observed, and deep coloring of F4 with a further smaller pore size was observed. As shown in (1-1), coloring of the filtrate was observed. These results demonstrate that, in the control, although the complex was not trapped on F1 and F2, a small amount of the complex was trapped on F3, and a large amount of the complex was trapped on F4, the complex partially passes through all of these filters, and the recovery leakage was generated. In contrast, as to the mixture containing $Na_2SO_4$ mixed therein so as to have a concentration of 2 mol/L, coloring of F1 and F2 with large pore sizes and F3 with a smaller pore size was observed, and coloring of F4 with a further smaller pore size was not observed, and as shown in (1-1), coloring of the filtrate was not observed. These results demonstrate that compared with the control in which a large amount of the complex was trapped on F4, the entire complex was trapped on the filters F1, F2, and F3 with larger pore sizes without generating the recovery leakage. Furthermore, as to the mixture containing $Na_2SO_4$ mixed therein so as to have a concentration of 3 mol/L, coloring of only F1 that is the first layer on the mixture introduction side was observed, coloring of the other filters was not observed, and as shown in (1-1), coloring of the filtrate was not observed. These results demonstrate that compared with the control in which a large amount of the complex was trapped on F4, the entire complex could be trapped on only the filter F1 with a larger pore size without generating the recovery leakage. These results demonstrate that the complex can be trapped on the filter with a larger pore size by causing the inorganic salt to be present together in the mixture of the metal and the chelating agent. Although it is assumed that the cause of this is an increase in size of the aggregate of the complex by the presence of the inorganic salt together, this assumption does not at all limit the present invention.

Example 2

It was demonstrated that the foaming of the mixture containing an urine sample and dithizone was suppressed by adding $Na_2SO_4$ as an inorganic salt.

Each mixture was prepared in the same manner as in Example 1 except that $Na_2SO_4$ was added to each of urine samples A to E collected from five subjects so as to have a concentration of 2 mol/L and was then shaken to form each complex. The mixture was then stood still at 24° C. for 5 minutes, and the mixture was thereafter subjected to visual observation to observe foaming. As a control, visual observation was performed in the same manner as described above except that the inorganic salt was not added.

Then, the height (H) of the foaming from the liquid level of the mixture was evaluated based on the following criteria. The evaluation results are shown in Table 3.

(Foaming Evaluation)
+60 mm<H
−40 mm≤H≤60 mm
−−H<40 mm

TABLE 3

| Inorganic salt | A | B | C | D | E |
|---|---|---|---|---|---|
| Non-addition (−) | + | + | + | + | + |
| $Na_2SO_4$ (+) | −− | −− | −− | −− | −− |

The results of the foaming evaluation are shown in Table 3. As shown in Table 3, the extent of foaming was low in the mixture containing $Na_2SO_4$ to be mixed therein so as to have a concentration of 2 mol/L in each of the samples A to E, compared with the control. This demonstrates that the foaming of the mixture containing an urine sample and dithizone can be suppressed by mixing an inorganic salt therein.

Example 3

It was demonstrated that variations in recovery yield of a complex between dithizone and a metal among samples could be suppressed by adding various inorganic salts.

With respect to urine samples collected from seven subjects, each complex was recovered by filtration with a filter under the condition where an inorganic salt was not added, and the complex recovery yield was determined. Specifically, the mixture was subjected to centrifugal filtration using a filter in the same manner as in (1-1) except that the inorganic salt was not added. Then, the mercury amounts in the complex of the mixture before the filtration and the filtrate obtained by the filtration were measured using cold vapor atomic absorption spectrometer (MERCURY ANALYZER, produced by Nippon Instruments, Co., Ltd.). Subsequently, the complex recovery yield by the filter was calculated according to the following formula (1).

$$\text{Complex recovery yield (\%)}=100\times[(M-F)/M] \quad (1)$$

M: Mercury amount in mixture
F: Mercury amount in filtrate

Furthermore, the filtrate of each sample was centrifuged, and the presence or absence of the complex leakage was observed by visual observation in the same manner as in (1-1).

The results demonstrate that there are samples in which the leakage was not observed by visual check and samples in which the leakage was observed by visual check among seven kinds of the samples. Thus, the former three samples (F to H) were classified into a sample group of not generating the recovery leakage, and the latter four samples (I to L) were classified into a sample group of generating the recovery leakage.

Subsequently, with respect to each of the sample group (F to H) of not generating the recovery leakage and the sample group (I to L) of generating the recovery leakage, the mixture containing an inorganic salt added thereto was filtrated with a filter, and the complex recovery yield was determined. As the inorganic salt, $Na_2SO_4$ or $(NH_4)_2SO_4$ was used. Specifically, the complex recovery yield was calculated, and the visual observation was performed, in the same manner as described above, except that the complex was formed in the mixture, and the inorganic salt was thereafter added thereto to have a concentration of 2.0 mol/L or 1.9 mol/L, and the mixture was then stood still.

Figure 2:
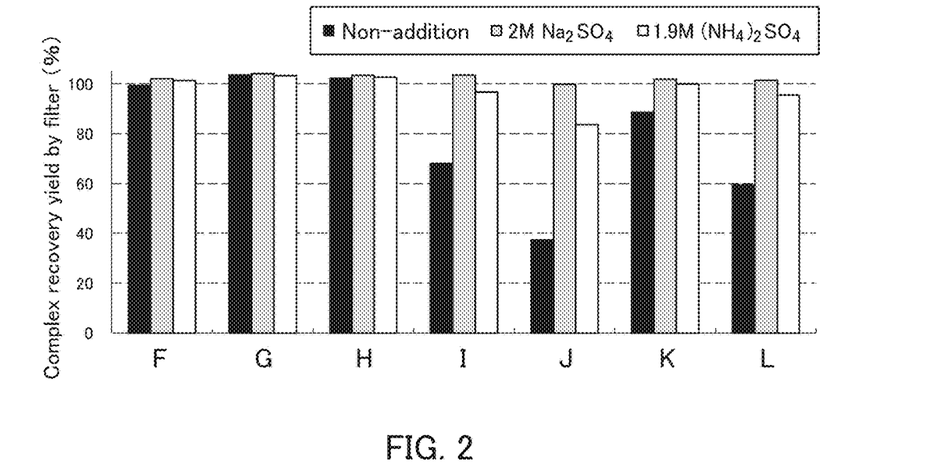
FIG. 2 is a graph showing the recovery yield of the complex by a filter in Example 3.

The results of these are shown in FIG. 2 and Table 4 together with the results in the case of non-addition of the inorganic salt. FIG. 2 is a graph showing the complex recovery yield. The horizontal axis indicates the sample name, and the vertical axis indicates the complex recovery yield. The black bar indicates the result in the case of non-addition of the inorganic salt, the gray bar indicates the result in the case of the addition of $Na_2SO_4$, and the white bar indicates the result in the case of addition of $(NH_4)_2SO_4$. Table 4 shows the presence or absence of the complex recovery leakage by visual observation. As shown in FIG. 2 and Table 4, the recovery leakage was prevented, and the recovery yields were significantly improved in the sample group (I to L) of generating the recovery leakage compared with the results in the case of non-addition of the inorganic salt. In the sample group (F to H) of not generating the complex recovery leakage, the complex leakage and the complex recovery yield were not affected by the addition of the inorganic salt, and the complex recovery leakage was not generated, and the complex recovery yields were not reduced as in the retuls of non-addition of the inorganic salt. This demonstrates that by filtrating the mixture containing the complex in the presence of the inorganic salt, the complex recovery leakage and the complex recovery yield are not affected in the sample group of not generating the recovery leakage, and the complex recovery leakage can be prevented, and the complex recovery yield can be improved in the sample group of generating the recovery leakage. These results demonstrate that variations in complex recovery yield among samples can be suppressed by filtrating the mixture in the presence of the inorganic salt.

TABLE 4

| Inorganic salt | The absence of complex leakage | | | The presence of complex leakage | | | |
|---|---|---|---|---|---|---|---|
| | F | G | H | I | J | K | L |
| Non-addition | − | − | − | + | + | + | + |
| $Na_2SO_4$ | − | − | − | − | − | − | − |
| $(NH_4)_2SO_4$ | − | − | − | − | − | − | − |

+: the presence of recovery leakage
−: the absence of recovery leakage

Example 4

It was demonstrated that a complex formed between dithizone and a metal could be recovered with a filter with a relatively large pore size by adding $(NH_4)_2SO_4$ as an inorganic salt.

The filters were observed by visual observation in the same manner as in (1-2) except that $(NH_4)_2SO_4$ as an inorganic salt was added to the mixture so as to have a concentration of 2, 3 or 5 mol/L. As to a control, visual observation was performed in the same manner as described above except that the inorganic salt was not added.

Figure 3:
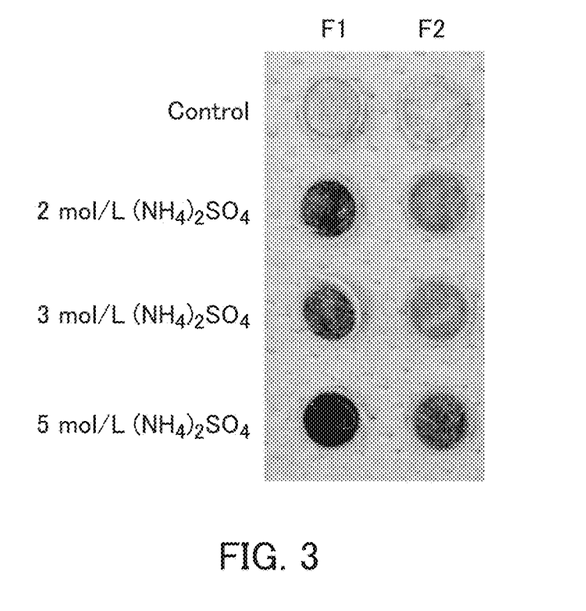
FIG. 3 is a photograph showing each filter after filtration in Example 4.

The results of these are shown in FIG. 3. FIG. 3 is a photograph obtained by taking the surface of each filter on the mixture introduction side. In FIG. 3, the left side of the photograph indicates the kind and the concentration of the inorganic salt, and the upper side of the photograph indicates the kind of each filter. In FIG. 3, the filters are arranged in order from the mixture introduction side to the mixture discharge side from the left side to the right side of the photograph. As shown in FIG. 3, as to the control, coloring of F1 and F2 (the same kind of filter) with a large pore size was not observed. These results demonstrate that the complex cannot be trapped on F1 and F2 in the control. In contrast, as to the mixture containing $(NH_4)_2SO_4$ added thereto, coloring of F1 and F2 with large pore sizes was observed. These results demonstrate that the complex can be trapped on a filter with a pore size relatively larger than the filter on which the complex was trapped in the absence of the inorganic salt by causing the inorganic salt to be present together in the mixture.

Example 5

It was demonstrated that the recovery yield of a complex between dithizone and a metal was improved by adding $Na_2SO_4$ as an inorganic salt.

Urine samples were classified into the sample of generating the recovery leakage and the sample of not generating the recovery leakage by the same method as in Example 3. Subsequently, with respect to each of the sample of generating the recovery leakage (n=1) and the sample of not generating the recovery leakage (n=1), the mixture was filtrated with a filter under the condition of addition or non-addition of the inorganic salt, and the complex recovery yield was calculated in the same manner as in Example 3. $Na_2SO_4$ was used as the inorganic salt, and the concentration thereof in the mixture was a predetermined concentration (0, 1, 2 or 3 mol/L).

Figure 4:
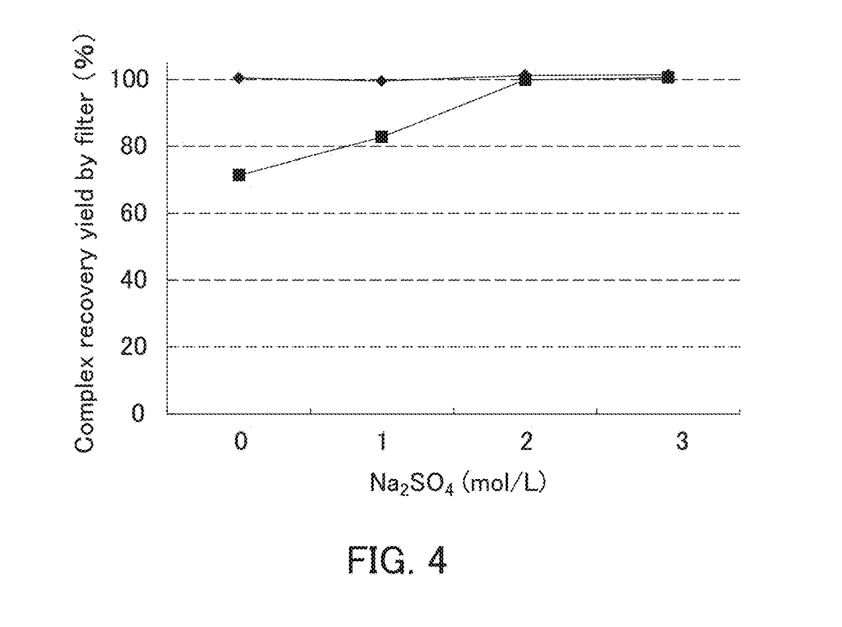
FIG. 4 is a graph showing the recovery yield of the complex by a filter in Example 5.

The results of these are shown in FIG. 4. FIG. 4 is a graph showing the complex recovery yield. The horizontal axis indicates the concentration of the inorganic salt, and the vertical axis indicates the complex recovery yield. A plot indicated by rhombuses indicates the sample of not generating the recovery leakage, and a plot indicated by squares indicates the sample of generating the recovery leakage. As shown in FIG. 4, as to the sample of generating the recovery leakage, the complex recovery yield was increased depending on the concentration of $Na_2SO_4$ by adding $Na_2SO_4$ and reached 100% at the concentration of 2 mol/L or more. Furthermore, as to the sample of not generating the recovery leakage, the recovery yield was not affected by adding $Na_2SO_4$ and was maintained to be 100%. These results demonstrate that the complex recovery yield can be improved by filtration with a filter in the presence of the inorganic salt.

Example 6

Complexes between dithizone and multiple metals were formed and recovered with addition of $Na_2SO_4$ as an inorganic salt. Then, it was demonstrated that the multiple metals could be recovered from the recovered complexes.

0.3 mL of 1 mol/L aqueous lithium hydroxide solution was added to 3 mL of an urine sample to adjust the pH of the urine sample to be an alkaline pH. 0.1 mg of dithizone was added to the urine sample after the pH adjustment, and the mixture thus obtained was then shaken with a shaker at 24° C. for 5 minutes to form a complex. Subsequently, 1 mol/L citric acid-sodium citrate buffer solution (pH2.0) was added thereto so that the pH of the mixture became pH 5.0. Thus, the complex became an insoluble complex. An inorganic salt was further added to the sample after the pH adjustment so as to have a concentration of 1.9 mol/L, which was then shaken at 24° C. for 10 minutes and left standing for 5 minutes. $Na_2SO_4$ was used as the inorganic salt.

The mixture containing the inorganic salt added thereto was further filtrated with a filter to recover the complex on the filter. 0.1 mL of 2 mol/L aqueous lithium hydroxide solution was added to the recovered complex, which was then stirred with suction and discharge so that the aqueous lithium hydroxide solution was permeated through the entire filter. Thus, the complex was dissolved in the aqueous lithium hydroxide solution. The solution thus obtained was then collected by pressurizing the filter.

Subsequently, the mercury amounts and the lead amounts in an unprocessed urine sample and the mixture were measured. The mercury amounts were measured using a cold vapor atomic absorption spectrometer. The lead amounts were msasured using a flameless atomic absorption spectrometer (iCE3400, produced by Thermo Fisher SCIENTIFIC). The mercury recovery yield and the lead recovery yield were then calculated according to the following formula (2). The results showed that the mercury recovery yield was 74.0%, and the lead recovery yield was 68.6%. These results demonstrate that multiple metals can be recovered with high recovery yields by the metal recovery method of the present invention.

$$\text{Recovery yield (\%)}=100\times(M/B) \quad (2)$$

M: Mercury or lead amount in solution

B: Mercury or lead amount in unprocessed urine sample

While the invention has been particularly shown and described with reference to exemplary embodiments and examples thereof, the invention is not limited to these embodiments and examples. It will be understood by those of ordinary skill in the art that various changes in form and details may be made therein without departing from the spirit and scope of the present invention as defined by the claims.

This application claims priority from Japanese Patent Application No. 2014-039592 filed on Feb. 28, 2014 and Japanese Patent Application No. 2015-036117 filed on Feb. 26, 2015, the entire subject matter of which are incorporated herein by reference.

INDUSTRIAL APPLICABILITY

According to the present invention, the variations in recovery yield among samples such as described above can be suppressed by suppressing the complex leakage. Moreover, as to a sample with a low recovery yield, the recovery yield can be improved, for example. Therefore, a metal can be analyzed with further superior reliability. Thus, the present invention is really useful in clinical examinations of samples derived from biological bodies and environmental testing, for example.

The invention claimed is:

1. A method for recovering a metal, the method comprising:
   mixing together a biological sample and a chelating agent to form a complex between the chelating agent and a metal present in the biological sample, where the mixture of the biological sample and the chelating agent is a substantially aqueous medium and solubility of the chelating agent in the mixture is different depending on the pH of the mixture;
   adding an inorganic salt to the mixture containing the complex;
   performing a pH adjustment such that the complex in the mixture remains undissolved; and
   filtrating the mixture containing the complex to recover the complex, thereby recovering the metal in the biological sample, wherein the pH is adjusted at any time before filtrating the mixture to recover the complex.

2. The method according to claim 1, wherein the inorganic salt is at least one of a chloride and a hydrosulfate.

3. The method according to claim 2, wherein the chloride is at least one selected from the group consisting of KCl, $MgCl_2$, and NaCl.

4. The method according to claim 2, wherein the hydrosulfate is at least one selected from the group consisting of $Na_2SO_4$, $(NH_4)_2SO_4$, and $K_2SO_4$.

5. The method according to claim 1, wherein in the metal recovering step,
   the concentration of the inorganic salt in the mixture is up to 8 mol/L.

6. The method according to claim 1, wherein the biological sample is urine.

7. The method according to claim 1, wherein the metal is at least one selected from the group consisting of Bi, Hg, Cd, Pd, Zn, Tl, Ag, Pb, As, and Al.

8. The method according to claim 1, wherein the chelating agent has a sulfur-containing group.

9. The method according to claim 1, wherein the chelating agent is 1,5-diphenyl-3-thiocarbazone.

10. The method according to claim 1, wherein in the complex forming step, the mixture further comprises a masking agent.

11. The method according to claim 10, wherein the masking agent is at least one selected from the group consisting of maleimide, N-methyl maleimide, N-ethyl maleimide, iodoacetamide, and iodoacetic acid.

12. A method for analyzing a metal, the method comprising:
   recovering a metal from a biological sample by the method according to claim 1; and
   analyzing the metal.

* * * * *

UNITED STATES PATENT AND TRADEMARK OFFICE
CERTIFICATE OF CORRECTION

PATENT NO. : 10,175,217 B2  
APPLICATION NO. : 14/632217  
DATED : January 8, 2019  
INVENTOR(S) : Akitsugu Kudo Page 1 of 1

It is certified that error appears in the above-identified patent and that said Letters Patent is hereby corrected as shown below:

On the Title Page

Item (54) and in the Specification, Column 1 Lines 1-2, should be corrected to read:  
Method for Recovering Metal and Metal Recovery Reagent Signed and Sealed this  
Second Day of July, 2019

Andrei Iancu  
*Director of the United States Patent and Trademark Office*